(12) United States Patent
Chatterton et al.

(10) Patent No.: US 9,114,152 B2
(45) Date of Patent: Aug. 25, 2015

(54) TRANSFERRIN/TRANSFERRIN RECEPTOR-MEDIATED SIRNA DELIVERY

(71) Applicant: Arrowhead Research Corporation, Pasadena, CA (US)

(72) Inventors: Jon E. Chatterton, Fort Worth, TX (US); Abbot F. Clark, Arlington, TX (US)

(73) Assignee: Arrowhead Research Corporation, Pasadena, CA (US)

( * ) Notice: Subject to any disclaimer, the term of this patent is extended or adjusted under 35 U.S.C. 154(b) by 88 days.

(21) Appl. No.: 13/765,216

(22) Filed: Feb. 12, 2013

(65) Prior Publication Data

US 2013/0177580 A1    Jul. 11, 2013

Related U.S. Application Data

(60) Division of application No. 13/112,635, filed on May 20, 2011, now Pat. No. 8,399,653, which is a continuation of application No. 12/244,027, filed on Oct. 2, 2008, now Pat. No. 7,973,019.

(60) Provisional application No. 60/977,272, filed on Oct. 3, 2007.

(51) Int. Cl.
*C07H 21/04*    (2006.01)
*C07K 16/00*    (2006.01)
*A61K 31/7088*   (2006.01)
*C12N 15/87*    (2006.01)

(52) U.S. Cl.
CPC ............ *A61K 31/7088* (2013.01); *C12N 15/87* (2013.01)

(58) Field of Classification Search
CPC ............................... C12N 15/113; A61K 48/00
See application file for complete search history.

(56) References Cited

U.S. PATENT DOCUMENTS

| 5,354,844 | A  | 10/1994 | Beug et al.      |
|-----------|----|---------|------------------|
| 5,670,151 | A  | 9/1997  | Larrick et al.   |
| 5,840,867 | A  | 11/1998 | Toole et al.     |
| 6,001,648 | A  | 12/1999 | McCall et al.    |
| 6,207,388 | B1 | 3/2001  | Grossman         |
| 6,225,058 | B1 | 5/2001  | Munishkin et al. |
| 6,372,250 | B1 | 4/2002  | Pardridge        |
| 6,632,671 | B2 | 10/2003 | Unger            |
| 7,973,019 | B1 | 7/2011  | Chatterton et al.|
| 8,399,653 | B2 | 3/2013  | Chatterton et al.|
| 2002/0001810 | A1 | 1/2002 | Farrell         |
| 2006/0014172 | A1 | 1/2006 | Muller et al.   |
| 2006/0040882 | A1 | 2/2006 | Chen et al.     |
| 2006/0166919 | A1 | 7/2006 | Shepard et al.  |
| 2006/0172961 | A1 | 8/2006 | Clark et al.    |
| 2006/0172963 | A1 | 8/2006 | Shepard et al.  |
| 2006/0172965 | A1 | 8/2006 | Shepard et al.  |
| 2006/0210527 | A1 | 9/2006 | Davis           |
| 2006/0223773 | A1 | 10/2006| Clark et al.    |
| 2007/0149473 | A1 | 6/2007 | Chatterton et al.|
| 2007/0155690 | A1 | 7/2007 | Chatterton et al.|
| 2007/0202076 | A1 | 8/2007 | Triche et al.   |
| 2007/0287681 | A1 | 12/2007| Jeong et al.    |
| 2009/0087494 | A1 | 4/2009 | Kompella et al. |

OTHER PUBLICATIONS

Bora, et al.; "Complement activation via alternative pathway is critical in the development of laser-induced choroidal neovascularization: role of Factor B and Factor H1"; Journal of Immunology; vol. 177; pp. 1872-1878; 2006.

Campochiaro; "Potential applications for RNAi to probe pathogenesis and develop new treatments for ocular disorders"; Gene Therapy; vol. 13; pp. 559-562; 2006.

Fire, et al.; "Potent and specific genetic interference by double-stranded RNA in caenorhabditis elegans"; Letters to Nature; Nature; vol. 391; pp. 806-811; Feb. 19, 1998.

Wadia, et al.; "Transducible TAT-HA fusogenic peptide enhances escape of TAT-fusion proteins after lipid raft macropinocytosis"; Technical Reports; Nature Medicine; vol. 10; No. 3; pp. 310-315; Mar. 2004.

Teh, et al.; "Identification of the epitope of a monoclonal antibody that disrupts binding of human transferrin to the human transferrin receptor"; the FEBS Journal; www.interscience.wiley.com/fulltext; pp. 1-9.

Song, et al.; "Antibody mediated in vivo delivery of small interfering RNAs via cell-surface receptors"; Nature Biotechnology; vol. 23; No. 6; pp. 709-717; Jun. 2005.

Qian, et al.; "Targeted drug delivery via the transferrin receptor-mediated endocytosis pathway"; Pharmacological Reviews; vol. 54; No. 4; pp. 561-587; 2002.

Liu, et al.; "Structural reorganization of the transferring C-lobe and transferrin receptor upon complex formation: The C-Lobe binds to the receptor helical domain"; Biochemistry; vol. 42; pp. 12447-12454; 2003.

Hu-Lieskovan, et al.; "Sequence-specific knockdown of EWS-FLI1 by targeted, nonviral delivery of small interferring RNA inhibits tumor growth in a murine model of metastatic ewing's sarcoma"; Cancer Research; vol. 65; No. 19; pp. 8984-8992; Oct. 1, 2005.

Chu, et al.; "Aptamer mediated siRNA delivery"; Nucleic Acids Research; vol. 34, No. 10; pp. e73; 2006.

Callens, et al.; "Recent advances in adult t-cell leukemia therapy: focus on a new anti-transferrin receptor monoclonal antibody"; Leukemia; vol. 22; pp. 42-48; 2008.

Kumar, et al.; "Transvascular delivery of small interfering RNA to the central nervous system"; Nature; vol. 448; pp. 39-43; Jul. 5, 2007.

Shen et al.; "Suppression of ocular neovascularization with siRNA Targeting VEGF Receptor 1"; Gene Therapy: vol. 13; pp. 225-234 (2006).

(Continued)

*Primary Examiner* — Amy Bowman

(57) ABSTRACT

The invention provides interfering RNA molecule-ligand conjugates useful as a delivery system for delivering interfering RNA molecules to a cell in vitro or in vivo. The conjugates comprise a ligand that can bind to a transferrin receptor (TfR). Therapeutic uses for the conjugates are also provided.

7 Claims, No Drawings

(56) References Cited

OTHER PUBLICATIONS

Reich et al.; "Small Interfering RNA (siRNA) Targeting VEGF Effectively Inhibits Ocular Neovascularization in a Mouse Model"; Molecular Vision; vol. 9; pp. 210-216 (2003).

Kim et al.; "Inhibition of Ocular Angiogenesis by siRNA Targeting Vascular Endothelial Growth Factor Pathway Genes"; Americal Journal of Pathology; vol. 165, No. 6; pp. 2177-2185 (2004).

Elbashir et al; "RNA Interference is Mediated by 21- and 22-Nucleotide RNAs"; Genes & Development; vol. 15; pp. 188-200 (2001).

Ikeda and Taira "Ligand-targeted delivery of therapeutic siRNA"; Expert Review; Pharmaceutical Research; vol. 23, No. 8; pp. 1631-1640; (Jul. 19, 2006).

Liu; "Exploring cell type-specific internalizing antibodies for targeted delivery of siRNA"; Briefings in Functional Genomics and Proteomics; vol. 6; No. 2; pp. 112-119; (Jul. 31, 2007).

TRANSFERRIN/TRANSFERRIN RECEPTOR-MEDIATED SIRNA DELIVERY

CROSS-REFERENCE TO RELATED APPLICATION

The present application is a divisional of U.S. patent application Ser. No. 13/112,635 filed May 20, 2011 (now allowed), which claims priority to U.S. patent application Ser. No. 12/244,027 filed Oct. 2, 2008 (now U.S. Pat. No. 7,973,019), which claims benefit to Provisional Patent Application No. 60/977,272 filed Oct. 3, 2007, the entire contents of which are incorporated herein by reference.

FIELD OF THE INVENTION

The invention relates to methods of delivering interfering RNA molecules to a cell via interfering RNA molecule-ligand conjugates. The conjugates comprise a ligand that can bind to a transferrin receptor (TfR). The invention also relates to methods for treating ocular disorders by administering an interfering RNA molecule-ligand conjugate of the invention to a patient in need thereof.

BACKGROUND OF THE INVENTION

RNA interference (RNAi) is a process by which double-stranded RNA (dsRNA) is used to silence gene expression. RNAi is induced by short (i.e. <30 nucleotide) double stranded RNA ("dsRNA") molecules which are present in the cell (Fire et al., 1998, Nature 391:806-811). These short dsRNA molecules called "short interfering RNA" or "siRNA," cause the destruction of messenger RNAs ("mRNAs") which share sequence homology with the siRNA (Elbashir et al., 2001, Genes Dev, 15:188-200). It is believed that one strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

RNAi provides a very exciting approach to treating and/or preventing diseases. Some major benefits of RNAi compared with various traditional therapeutic approaches include: the ability of RNAi to target a very particular gene involved in the disease process with high specificity, thereby reducing or eliminating off target effects; RNAi is a normal cellular process leading to a highly specific RNA degradation; and RNAi does not trigger a host immune response as in many antibody based therapies.

Several interfering RNA delivery methods are being tested/developed for in vivo use. For example, siRNAs can be delivered "naked" in saline solution; complexed with polycations, cationic lipids/lipid transfection reagents, or cationic peptides; as components of defined molecular conjugates (e.g., cholesterol-modified siRNA, TAT-DRBD/siRNA complexes); as components of liposomes; and as components of nanoparticles. These approaches have shown varying degrees of success. Thus, there is a need for new and improved methods for delivering siRNA molecules in vivo to achieve and enhance the therapeutic potential of RNAi.

SUMMARY OF THE INVENTION

The invention provides interfering RNA molecule-ligand conjugates, wherein the ligand can bind to a transferrin receptor (TfR). The invention also provides methods of using the conjugates for delivering an interfering RNA molecule into a cell in vitro or in vivo. In one aspect, an interfering RNA molecule-ligand conjugate of the invention can be used deliver an interfering RNA molecule to an eye of a patient.

The invention further provides methods of treating or preventing an ocular disorder in a patient, comprising administering to the patient an interfering RNA molecule-ligand conjugate, wherein the ligand can bind to a transferrin receptor (TfR) and wherein the interfering RNA molecule can attenuate expression of a gene associated with the ocular disorder. In certain aspects, the ocular disorder is associated with ocular angiogenesis, dry eye, ocular inflammatory conditions, ocular hypertension, or glaucoma. In other aspects, the conjugate is administered by intraocular injection, subconjunctival injection, intravitreal injection, anterior or posterior juxtascleral injection, topical ocular application, intravenous injection, oral administration, intramuscular injection, intraperitoneal injection, transdermal application, intranasal application, or transmucosal application.

Specific preferred embodiments of the invention will become evident from the following more detailed description of certain preferred embodiments and the claims.

DETAILED DESCRIPTION OF THE INVENTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides interfering RNA-ligand conjugates that can deliver interfering RNAs into an eye cell of a patient. In a particular embodiment, the conjugates can bind to a transferrin receptor (TfR) on the surface of an eye cell. The transferrin receptor is an integral membrane glycoprotein that mediates the uptake of iron by individual cells. There appears to be a correlation between the number of receptors on the surface of a cell and cellular proliferation, with the highest number of receptors being on actively growing cells and the lowest number being on resting and terminally differentiated cells.

The term "receptor" as used herein is intended to encompass the entire receptor or ligand-binding portions thereof. These portions of the receptor particularly include those regions sufficient for specific binding of the ligand to occur.

The ligand of the conjugate can be any molecule that is capable of binding with specificity to the transferrin receptor on cells of the eye. Examples of molecules include, but are not limited to, proteins and aptamers.

The term "protein" as used herein includes peptides, polypeptides, consensus molecules, fusion proteins, purified naturally occurring proteins, artificially synthesized proteins, antibodies, and analogs, derivatives or combinations thereof.

The term "aptamer" as used herein refers to nucleic acids (typically DNA, RNA or oligonucleotides) that are capable of binding to a particular molecular target. Aptamers emerge from in vitro selections or other types of aptamer selection procedures well known in the art (e.g. bead-based selection with flow cytometry or high density aptamer arrays) when the nucleic acid is added to mixtures of target molecules. An aptamer is typically between 10 and 300 nucleotides in length. RNA and DNA aptamers can be generated from in vitro selection experiments such as SELEX (Systematic Evolution of Ligands by Exponential Enrichment). Examples of aptamer uses and methods for making/selecting aptamers are described, for example, in Chu et al., 2006, *Nucl. Acids Res.* 34:e73), U.S. Patent Publication No. 20060014172, U.S. Pat. Nos. 5,840,867, 6,001,648, 6225,058, 6,207,388, and U.S. Patent Publication No. 20020001810, the disclosures of all of which are incorporated by reference in their entireties.

A particularly preferred ligand family includes peptides comprising the TfR-binding domain of transferrin (Tf), which is the nominal TfR ligand. In certain embodiments, the ligand is full length Tf, a less than full length Tf protein that comprises a TfR binding domain, or the C-lobe of Tf or a TfR-binding portion thereof.

Monoclonal antibody binding (Teh et al. *FEBS J.* 272: 6344-6353, 2005) and hydroxyl radical-mediated protein footprinting (Liu et al. *Biochemistry* 42:12447-12454, 2003) suggest that the TfR-binding domain of Tf is located within the C-lobe, residues 334-679 of human Tf. Residues 365-401 (especially 381-401), 415-433, and 457-470 appear to be particularly important for receptor binding.

An interfering RNA molecule can be covalently linked to a TfR-binding domain either directly or via a spacer, such as a glycine spacer of 1, 2, 3, or 4 glycines. Preferably, a glycine spacer is 2 or 3 glycines.

Other examples of ligands that can bind with specificity to TfR include antibodies or antibody fragments that can bind TfR. These antibodies or antibody fragments are as capable of binding to TfR as the nominal receptor ligand. Upon binding of the antibodies to TfR on a cell surface, transfer of the antibody and the attached interfering RNA into the cell occurs. The interfering RNA can be attached by any acceptable means for joining the antibody to the interfering RNA such that the interfering RNA can be transferred across the cell membrane in a pharmaceutically active form. In a preferred embodiment, the TfR-specific antibody or antibody fragment forms a conjugate with the interfering RNA.

In other embodiments, a TfR-specific antibody or antibody fragment and a second ligand, which is also reactive with the TfR, are joined together to form a fusion protein. The second ligand can be a second antibody or, more preferably, a nominal ligand such as transferrin, or a TfR binding fragment thereof. These fusion proteins have the advantage of possessing the capacity of interacting twice as readily with ocular cells than conjugates that only have one ligand.

Antibodies that can be used in this invention are reactive with a transferrin receptor on an eye cell. The term antibody is intended to encompass both polyclonal and monoclonal antibodies. The term antibody is also intended to encompass mixtures of more than one antibody reactive with a transferrin receptor (e.g., a cocktail of different types of monoclonal antibodies reactive with the TfR), each of which is joined to an interfering RNA to form a conjugate. The term antibody is further intended to encompass whole antibodies, biologically functional fragments thereof, fully humanized antibodies, and chimeric antibodies comprising portions from more than one species, bifunctional antibodies, etc. Biologically functional antibody fragments which can be used are those fragments which can be used for binding of the antibody fragment to the TfR to occur. Examples of TfR antibodies are described, for example, in Callens et al. (Leukemia, 27 Sep. 2007 epub ahead of print) and Qian et al. (Pharmacol. Rev. 54:561-587, 2002).

The interfering RNA can be linked to a ligand using chemical conjugation techniques. In addition to covalent bonding, conjugates can be formed employing non-covalent bonds, such as those formed with bifunctional antibodies, ionic bonds, hydrogen bonds, hydrophobic interactions, etc.

In certain embodiments, an interfering RNA-ligand conjugate of the invention can further comprise a nucleic acid binding protein, such as protamine, covalently linked to the ligand. For example, the ligand of the conjugate can comprise a transferrin peptide-protamine fusion protein or a TfR-specific antibody-protamine fusion protein. Antibody-protamine fusion proteins have been used to deliver siRNA to HIV-infected or envelope-transfected cells (Song et al., 2005, *Nat. Biotechnol.* 23:709-717). The interfering RNA molecule can be linked to the ligand via interaction with the nucleic acid binding protein.

In other embodiments, the ligand of the interfering RNA-ligand conjugate of the invention is covalently linked to a polycation, such as polylysine. For example, the conjugate can comprise a transferrin peptide fused to polylysine or another polycation, or a TfR-specific antibody fused to polylysine or another polycation, such as polyarginine or polyethyleneimine (PEI). Methods for preparing and delivering nucleic acids to a variety of cultured mammalian cells and to tumor-bearing mice using transferrin-polycation-DNA conjugates have been described (reviewed in Qian, et al., 2002, *Pharmacol Rev* 54:561-587). The interfering RNA molecule can be linked to the ligand via interaction with the polycation.

In certain embodiments, the interfering RNA molecule is linked to the ligand via a peptide consisting entirely of arginines (referred to herein as an "Arg peptide"). Preferably, the Arg peptide comprises 7 arginines (7×Arg), 8 arginines (8×Arg), 9 arginines (9×Arg), 10 arginines (10×Arg), or 11 (11×Arg) arginines. The Arg peptide can be linked to the C- or N-terminus of a ligand, such as the TfR-binding domain, via a glycine spacer of 1 to 4 glycines. Preferably, the glycine spacer is 2 or 3 glycines.

In one embodiment, the Arg peptide is a 9×Arg peptide. In one embodiment, the 9×Arg peptide comprises or consists of D-isomers. In a particular embodiment, the "9×Arg peptide" as used herein means a peptide of 9 arginine residues (R$^\dagger$R'R'R'R'R'R'R'R'; SEQ ID NO: 1). Negatively charged interfering RNA molecules can bind to the positively charged 9×Arg peptide as described in Kumar et al., who recently demonstrated that a 9×Arg peptide could be used to link interfering RNA molecules to the C-terminal end of a rabies virus glycoprotein (RVG) targeting peptide for delivery across the blood-brain barrier (Kumar et al., Jun. 17, 2007, Nature, epub ahead of print).

In certain embodiments, an interfering RNA-ligand conjugate is administered to a patient or a cell in the presence of a TAT-HA2 peptide, a ligand-HA2 peptide, or a retro-inverso (i.e., the reverse sequence constructed of D-amino acids) TAT-HA2 peptide, which has been shown to enhance release of peptide/protein conjugates from the endosome (Wadia et al., 2004, Nat. Med. 10:310). The term "HA2 peptide" means a peptide comprising the N-terminal 20 amino acids of influenza virus hemagglutinin protein. The native HA2 peptide is:

SEQ ID NO: 2
GLFGAIAGFIENGWEGMIDG;.

Preferably, the native HA2 peptide comprises L-isomers. The retro-inverso HA2 peptide is:

SEQ ID NO: 3
GD†I†M†GE†W†GN†E†I†F†GA†I†A†GF†L†G;.

D-isomers are denoted by a superscripted dagger (†) to the right of the one-letter code symbol; thus, D† represents D-aspartic acid and L† represents D-leucine.

The presence of HA2 aids release of the interfering RNA delivery system from the endosome into the cytosol, so that the interfering RNA molecular can attenuate expression of a target mRNA in a cell. In certain other embodiments, an HA2 peptide is inserted between the TfR ligand and the 9×Arg, wherein the HA2 peptide is linked to the ligand and 9×Arg via glycine spacers. One example of a ligand-HA2 conjugate is as follows:

SEQ ID NO: 4
Ligand-GGGD†I†M†GE†W†GN†E†I†F†GA†I†A†GF†L†GGG

R†R†R†R†R†R†R†R†R†;.

In certain embodiments, the TfR ligand-9×Arg peptide is produced as a single peptide before being conjugated to the interfering RNA molecule. In other embodiments, the TfR ligand-9×Arg peptide can be produced by combining the TfR ligand and the 9×Arg peptide under conditions in which the ligand and the peptide will connect to each other. Such methods for linking two peptides are well known in the art. In yet other embodiments, the 9×Arg peptide can be premixed with the interfering RNA molecule and then linked to the TfR ligand to favor binding of the interfering RNA to the 9×Arg end of the peptide. Thus, linkage of the interfering RNA molecule can be accomplished before or after linkage of TfR ligand with 9×Arg.

In certain embodiments, the invention provides a method of attenuating expression of a target mRNA in an eye of a patient, comprising (a) providing an interfering RNA-ligand conjugate, wherein the conjugate binds to a transferrin receptor (TfR); and (b) administering the conjugate to an eye of the patient, wherein the interfering RNA molecule can attenuate expression of the target mRNA in the eye.

In certain embodiments, the invention provides a method of preventing or treating an ocular disorder in a patient, the method comprising administering to the patient an interfering RNA-ligand conjugate, wherein the conjugate binds to a TfR and transports said interfering RNA into an eye cell of the patient.

The term "patient" as used herein means a human or other mammal having an ocular disorder or at risk of having an ocular disorder. Ocular structures associated with such disorders may include the eye, retina, choroid, lens, cornea, trabecular meshwork (TM), iris, optic nerve, optic nerve head, sclera, anterior or posterior segment, or ciliary body, for example. In certain embodiments, a patient has an ocular disorder associated with TM cells, ciliary epithelium cells, or another cell type in the eye.

The term "ocular disorder" as used herein includes conditions associated with ocular angiogenesis, dry eye, inflammatory conditions, ocular hypertension and ocular diseases associated with elevated intraocular pressure (TOP), such as glaucoma.

The term "ocular angiogenesis," as used herein, includes ocular pre-angiogenic conditions and ocular angiogenic conditions, and includes those cellular changes resulting from the expression of certain genes that lead directly or indirectly to ocular angiogenesis, ocular neovascularization, retinal edema, diabetic retinopathy, sequela associated with retinal ischemia, posterior segment neovascularization (PSNV), and neovascular glaucoma, for example. The interfering RNAs used in a method of the invention are useful for treating patients with ocular angiogenesis, ocular neovascularization, retinal edema, diabetic retinopathy, sequela associated with retinal ischemia, posterior segment neovascularization (PSNV), and neovascular glaucoma, or patients at risk of developing such conditions, for example. The term "ocular neovascularization" includes age-related macular degeneration, cataract, acute ischemic optic neuropathy (AION), commotio retinae, retinal detachment, retinal tears or holes, iatrogenic retinopathy and other ischemic retinopathies or optic neuropathies, myopia, retinitis pigmentosa, and/or the like.

The term "inflammatory condition," as used herein, includes conditions such as ocular inflammation, allergic conjunctivitis, dermatitis, rhinitis, and asthma.

The methods of the invention are useful for attenuating expression of particular genes in the eyes of patients using RNA interference.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of delivering interfering RNA to inhibit the expression of a target mRNA thus decreasing target mRNA levels in patients with ocular disorders.

The phrase "attenuating expression" with reference to a gene or an mRNA as used herein means administering or expressing an amount of interfering RNA (e.g., an siRNA) to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of a target gene by an interfering RNA molecule of the invention can be inferred in a human or other mammal by observing an improvement in symptoms of the ocular disorder, including, for example, a decrease in intraocular pressure that would indicate inhibition of a glaucoma target gene.

In one embodiment, a single interfering RNA is delivered to decrease target mRNA levels. In other embodiments, two or more interfering RNAs targeting the mRNA are administered to decrease target mRNA levels. The interfering RNAs may be delivered in the same interfering RNA molecule-ligand conjugate or in separate conjugates.

As used herein, the terms "interfering RNA" and "interfering RNA molecule" refer to all RNA or RNA-like molecules that can interact with RISC and participate in RISC-mediated changes in gene expression. Examples of other interfering RNA molecules that can interact with RISC include siRNAs, short hairpin RNAs (shRNAs), single-stranded siRNAs, microRNAs (miRNAs), and dicer-substrate 27-mer duplexes. Examples of "RNA-like" molecules that can interact with RISC include siRNA, single-stranded siRNA, microRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, and dicer-substrate 27-mer duplexes are subsets of "interfering RNAs" or "interfering RNA molecules."

The term "siRNA" as used herein refers to a double-stranded interfering RNA unless otherwise noted. Typically, an siRNA used in a method of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). Typically, an interfering RNA used in a method of the invention has a length of about 19 to 49 nucleotides. The phrase "length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

Single-stranded interfering RNA has been found to effect mRNA silencing, albeit less efficiently than double-stranded RNA. Therefore, embodiments of the present invention also provide for administration of a single-stranded interfering RNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 5' or 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

In certain embodiments, an interfering molecule of the invention comprises at least one of the modifications as described above.

The phrases "target sequence" and "target mRNA" as used herein refer to the mRNA or the portion of the mRNA sequence that can be recognized by an interfering RNA used in a method of the invention, whereby the interfering RNA can silence gene expression as discussed herein. Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Interfering RNA target sequences (e.g., siRNA target sequences) within a target mRNA sequence are selected using available design tools as described above. Interfering RNAs corresponding to a target sequence are then tested in vitro by transfection of cells expressing the target mRNA followed by assessment of knockdown as described herein. The interfering RNAs can be further evaluated in vivo using animal models as described herein.

The ability of interfering RNA to knock-down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression. Human corneal epithelial cells, trabecular meshwork cells, ciliary epithelial cells, retinal pigment epithelial cells, or other human ocular cell lines may also be use for an evaluation of the ability of interfering RNA to knock-down levels of an endogenous target gene.

A number of animal models are known that can be used to test the activity of an interfering RNA molecule. For example, siRNA molecules can be tested in murine laser-induced models of choroidal neovascularization (CNV) as described in Reich et al., 2003, *Mol. Vision.* 9:210-216; Shen et al., 2006, *Gene Therapy* 13:225-234; or Bora et al., 2006, *J. Immunol.* 177:1872-1878.

In certain embodiments, an interfering RNA molecule-ligand conjugate comprises an interfering RNA molecule that targets a gene associated with an ocular disorder. Examples of mRNA target genes for which interfering RNAs of the present invention are designed to target include genes associated with the disorders that affect the retina, genes associated with glaucoma, and genes associated with ocular inflammation.

Examples of mRNA target genes associated with the retinal disorders include tyrosine kinase, endothelial (TEK); complement factor B (CFB); hypoxia-inducible factor 1, α subunit (HIF1A); HtrA serine peptidase 1 (HTRA1); platelet-derived growth factor receptor β (PDGFRB); chemokine, CXC motif, receptor 4 (CXCR4); insulin-like growth factor I receptor (IGF1R); angiopoietin 2 (ANGPT2); v-fos FBJ murine osteosarcoma viral oncogene homolog (FOS); cathepsin L1, transcript variant 1 (CTSL1); cathepsin L1, transcript variant 2 (CTSL2); intracellular adhesion molecule 1 (ICAM1); insulin-like growth factor I (IGF1); integrin α5 (ITGAS); integrin β1 (ITGB1); nuclear factor kappa-B, subunit 1 (NFKB1); nuclear factor kappa-B, subunit 2 (NFKB2); chemokine, CXC motif, ligand 12 (CXCL12); tumor necrosis factor-alpha-converting enzyme (TACE); tumor necrosis factor receptor 1 (TNFR1); vascular endothelial growth factor (VEGF); vascular endothelial growth factor receptor 1 (VEGFR1); and kinase insert domain receptor (KDR).

Examples of target genes associated with glaucoma include carbonic anhydrase II (CA2); carbonic anhydrase IV (CA4); carbonic anhydrase XII (CA12); β1 andrenergic receptor (ADBR1); β2 andrenergic receptor (ADBR2); acetylcholinesterase (ACHE); Na+/K+− ATPase; solute carrier family 12 (sodium/potassium/chloride transporters), member 1 (SLC12A1); solute carrier family 12 (sodium/potassium/chloride transporters), member 2 (SLC12A2); connective tissue growth factor (CTGF); serum amyloid A (SAA); secreted frizzled-related protein 1 (sFRP1); gremlin (GREM1); lysyl oxidase (LOX); c-Maf; rho-associated coiled-coil-containing protein kinase 1 (ROCK1); rho-associated coiled-coil-containing protein kinase 2 (ROCK2); plasminogen activator inhibitor 1 (PAI-1); endothelial differentiation, sphingolipid G-protein-coupled receptor, 3 (Edg3 R); myocilin (MYOC); NADPH oxidase 4 (NOX4); Protein Kinase Cδ (PKCδ); Aquaporin 1 (AQP1); Aquaporin 4 (AQP4); members of the complement cascade; ATPase, H+ transporting, lysosomal V1 subunit A (ATP6V1A); gap junction protein α-1 (GJA1); formyl peptide receptor 1 (FPR1); formyl peptide receptor-like 1 (FPRL1); interleukin 8 (IL8); nuclear factor kappa-B, subunit 1 (NFKB1); nuclear factor kappa-B, subunit 2 (NFKB2); presenilin 1 (PSEN1); tumor necrosis factor-alpha-converting enzyme (TACE); transforming growth factor β2 (TGFB2); transient receptor potential cation channel, subfamily V, member 1 (TRPV1); chloride channel 3 (CLCN3); gap junction protein α5 (GJAS); tumor necrosis factor receptor 1 (TNFR1); and chitinase 3-like 2 (CHI3L2).

Examples of mRNA target genes associated with ocular inflammation include tumor necrosis factor receptor superfamily, member 1A (TNFRSF1A); phosphodiesterase 4D, cAMP-specific (PDE4D); histamine receptor H1 (HRH1); spleen tyrosine kinase (SYK); interkeukin 1β (IL1B); nuclear factor kappa-B, subunit 1 (NFKB1); nuclear factor kappa-B, subunit 2 (NFKB2); and tumor necrosis factor-alpha-converting enzyme (TACE).

Such target genes are described, for example, in U.S. Patent Applications having Publication Nos. 20060166919, 20060172961, 20060172963, 20060172965, 20060223773, 20070149473, and 20070155690, the disclosures of which are incorporated by reference in their entirety.

In other embodiments, the method of delivering an interfering RNA molecule comprises administering to the patient a nanoparticle-ligand conjugate, wherein the interfering RNA molecule is encapsulated in the nanoparticle and the nanoparticle is linked to a ligand that can bind to the transferrin receptor, which transports the interfering RNA molecule into an eye cell of the patient. Other embodiments of the invention provide a method of preventing or treating an ocular disorder, said method comprising delivering an interfering RNA molecule to the eye of a patient using a nanoparticle-ligand conjugate. Methods for preparing nanoparticles and their use in delivering pharmaceutical agents have been described in U.S. Pat. No. 6,632,671, the disclosures of which are incorporated by reference in their entirety. Methods for preparing nanoparticle-ligand conjugates and their use in delivering pharmaceutical agents have been described in U.S. Pat. No. 6,372,250, the disclosures of which are incorporated by reference in their entirety.

The interfering RNA-ligand conjugates and nanoparticle-ligand conjugates can be administered by intraocular injection, ocular topical application, intravenous injection, oral administration, intramuscular injection, intraperitoneal injection, transdermal application, or transmucosal application. The form and concentration in which the conjugate is administered (e.g., capsule, tablet, solution, emulsion) will depend at least in part on the route by which it is administered.

In certain embodiments, the method of treating an ocular disease involves an ocular disease associated with trabecular meshwork (TM) cells, ciliary epithelium cells, or another cell type of the eye.

In certain embodiments, the invention provides an ocular pharmaceutical composition for preventing or treating an ocular disorder in a patient, comprising an interfering RNA-ligand conjugate or nanoparticle-ligand conjugate of the invention in an ophthalmically acceptable carrier and in a therapeutically effective amount.

Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Interfering RNA-ligand conjugates and nanoparticle-ligand conjugates of the present invention are administered as solutions, suspensions, or emulsions. The following are examples of pharmaceutical composition formulations that may be used in the methods of the invention.

|  | Amount in weight % |
| --- | --- |
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

|  | Amount in weight % |
| --- | --- |
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
| --- | --- |
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

|  | Amount in weight % |
| --- | --- |
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein, the term "therapeutically effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

Generally, a therapeutically effective amount of the interfering RNAs used in a composition of the invention results in an extracellular concentration at the surface of the target cell of from 100 pM to 1 μM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ, such as the eye, one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 4.5 to about pH 7.4.

A therapeutically effective amount of a formulation may depend on factors such as the age, race, and sex of the subject, the severity of the disorder, the rate of target gene transcript/protein turnover, the interfering RNA potency, and the interfering RNA stability, for example. In one embodiment, the interfering RNA is delivered topically to a target organ and reaches the target mRNA-containing tissue such as the trabecular meshwork, retina or optic nerve head at a therapeutic dose thereby ameliorating target gene-associated disease process.

Therapeutic treatment of patients with interfering RNAs directed against target mRNAs is expected to be beneficial over small molecule treatments by increasing the duration of action, thereby allowing less frequent dosing and greater patient compliance, and by increasing target specificity, thereby reducing side effects.

An "ophthalmically acceptable carrier" as used herein refers to those carriers that cause at most, little to no ocular irritation, provide suitable preservation if needed, and deliver one or more interfering RNAs of the present invention in a homogenous dosage.

The interfering RNA-ligand conjugates and nanoparticle-ligand conjugates may be delivered in solution, in suspension, or in bioerodible or non-bioerodible delivery devices.

Interfering RNA-ligand conjugates and nanoparticle-ligand conjugates may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

In certain embodiments, treatment of ocular disorders with interfering RNA molecules is accomplished by administration of an interfering RNA-ligand conjugate or nanoparticle-ligand conjugate directly to the eye. Local administration to the eye is advantageous for a number or reasons, including: the dose can be smaller than for systemic delivery, and there is less chance of the molecules silencing the gene target in tissues other than in the eye.

A number of studies have shown successful and effective in vivo delivery of interfering RNA molecules to the eye. For example, Kim et al. demonstrated that subconjunctival injection and systemic delivery of siRNAs targeting VEGF pathway genes inhibited angiogenesis in a mouse eye (Kim et al., 2004, *Am. J. Pathol.* 165:2177-2185). In addition, studies have shown that siRNA delivered to the vitreous cavity can diffuse throughout the eye, and is detectable up to five days after injection (Campochiaro, 2006, *Gene Therapy* 13:559-562).

Interfering RNA-ligand conjugates and nanoparticle-ligand conjugates may be delivered directly to the eye by ocular tissue injection such as periocular, conjunctival, subtenon, intracameral, intravitreal, intraocular, anterior or posterior juxtascleral, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, interfering RNA-ligand conjugates and nanoparticle-ligand conjugates may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the conjugate in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA-ligand conjugate or nanoparticle-ligand conjugate is combined with a preservative in an appropriate vehicle, such as mineral oil, liquid lanolin, or white petrolatum. Sterile ophthalmic gel formulations may be prepared by suspending the interfering RNA-ligand conjugate or nanoparticle-ligand conjugate in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

In certain embodiments, the invention also provides a kit that includes reagents for attenuating the expression of an mRNA as cited herein in a cell. The kit contains an interfering RNA molecule-ligand conjugate and/or the necessary components for interfering RNA molecule-ligand conjugate production (e.g., an interfering RNA molecule as well as the ligand and necessary materials for linking). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and a ligand. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

It should be understood that the foregoing disclosure emphasizes certain specific embodiments of the invention and that all modifications or alternatives equivalent thereto are within the spirit and scope of the invention as set forth in the appended claims.

What is claimed is:

1. An interfering RNA molecule-ligand conjugate, wherein the ligand is linked to the peptide consisting of SEQ ID NO: 3, and wherein the ligand can bind to a transferrin receptor (TfR).

2. The interfering RNA molecule-ligand conjugate of claim 1, wherein the ligand comprises a TfR binding domain of transferrin.

3. The interfering RNA molecule-ligand conjugate of claim 2, wherein the ligand comprises the Tf C-lobe or a TfR-binding portion thereof.

4. The interfering RNA molecule-ligand conjugate of claim 1, wherein the interfering RNA molecule is linked to the ligand via a 7×Arg peptide, 8×Arg peptide, 9×Arg peptide, 10×Arg peptide, or 11×Arg peptide.

5. The interfering RNA molecule-ligand conjugate of claim 4, wherein the interfering RNA molecule is linked to the ligand via a 9×Arg peptide.

6. The interfering RNA molecule-ligand conjugate of claim 1, wherein the interfering RNA molecule is a siRNA, miRNA, or shRNA.

7. A pharmaceutical composition comprising the interfering RNA molecule-ligand conjugate of claim 1.

* * * * *

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(9)
<223> OTHER INFORMATION: D-isomers

<400> SEQUENCE: 1

Arg Arg Arg Arg Arg Arg Arg Arg Arg
1               5

<210> SEQ ID NO 2
<211> LENGTH: 20
<212> TYPE: PRT
<213> ORGANISM: Artificial
<220> FEATURE:
<223> OTHER INFORMATION: Synthetic peptide

<400> SEQUENCE: 2

Gly Leu Phe Gly Ala Ile Ala Gly Phe Ile Glu Asn Gly Trp Glu Gly
1               5                   10                  15

Met Ile Asp Gly
            20

<210> SEQ ID NO 3
<211> LENGTH: 20
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(4)
<223> OTHER INFORMATION: D-isomers
<220> FEATURE:
<221> NAME/KEY: MISC_FEATURE
<222> LOCATION: (6)..(7)
<223> OTHER INFORMATION: D-isomers
<220> FEATURE:
<221> NAME/KEY: MISC_FEATURE
<222> LOCATION: (9)..(12)
<223> OTHER INFORMATION: D-isomers
<220> FEATURE:
<221> NAME/KEY: MISC_FEATURE
<222> LOCATION: (14)..(16)
<223> OTHER INFORMATION: D-isomers
<220> FEATURE:
<221> NAME/KEY: MISC_FEATURE
<222> LOCATION: (18)..(19)
<223> OTHER INFORMATION: D-isomers

<400> SEQUENCE: 3

Gly Asp Ile Met Gly Glu Trp Gly Asn Glu Ile Phe Gly Ala Ile Ala
1               5                   10                  15
```

```
Gly Phe Leu Gly
            20

<210> SEQ ID NO 4
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(6)
<223> OTHER INFORMATION: D-siomers
<220> FEATURE:
<221> NAME/KEY: MISC_FEATURE
<222> LOCATION: (8)..(9)
<223> OTHER INFORMATION: D-siomers
<220> FEATURE:
<221> NAME/KEY: MISC_FEATURE
<222> LOCATION: (11)..(14)
<223> OTHER INFORMATION: D-siomers
<220> FEATURE:
<221> NAME/KEY: MISC_FEATURE
<222> LOCATION: (16)..(18)
<223> OTHER INFORMATION: D-siomers
<220> FEATURE:
<221> NAME/KEY: MISC_FEATURE
<222> LOCATION: (20)..(21)
<223> OTHER INFORMATION: D-siomers
<220> FEATURE:
<221> NAME/KEY: MISC_FEATURE
<222> LOCATION: (25)..(33)
<223> OTHER INFORMATION: D-siomers

<400> SEQUENCE: 4

Gly Gly Gly Asp Ile Met Gly Glu Trp Gly Asn Glu Ile Phe Gly Ala
1               5                   10                  15

Ile Ala Gly Phe Leu Gly Gly Gly Arg Arg Arg Arg Arg Arg Arg
            20                  25                  30

Arg
```